(12) United States Patent
Garabedian et al.

(10) Patent No.: US 11,344,357 B2
(45) Date of Patent: May 31, 2022

(54) TISSUE TREATMENT SYSTEM AND METHOD FOR TISSUE PERFUSION USING FEEDBACK CONTROL

(71) Applicant: Boston Scientific Scimed, Inc., Maple Grove, MN (US)

(72) Inventors: Robert J. Garabedian, Mountain View, CA (US); Amy C. Kelly, San Francisco, CA (US); Steve K. Landreville, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 231 days.

(21) Appl. No.: 15/667,695

(22) Filed: Aug. 3, 2017

(65) Prior Publication Data

US 2017/0325870 A1 Nov. 16, 2017

Related U.S. Application Data

(63) Continuation of application No. 12/037,882, filed on Feb. 26, 2008, now Pat. No. 9,757,188, which is a
(Continued)

(51) Int. Cl.
*A61B 18/14* (2006.01)
*A61B 18/02* (2006.01)
(Continued)

(52) U.S. Cl.
CPC .......... *A61B 18/0206* (2013.01); *A61B 18/12* (2013.01); *A61B 18/148* (2013.01);
(Continued)

(58) Field of Classification Search
CPC ..... A61B 18/12; A61B 18/14; A61B 18/1402; A61B 18/1477; A61B 18/1482;
(Continued)

(56) References Cited

U.S. PATENT DOCUMENTS

| 3,800,552 A | 4/1974 | Bulat et al. |
| 5,279,569 A | 1/1994 | Neer et al. |

(Continued)

FOREIGN PATENT DOCUMENTS

| DE | 4007295 | 9/1991 |
| EP | 0315444 | 5/1989 |

(Continued)

OTHER PUBLICATIONS

"File History," for U.S. Appl. No. 10/740,692.
(Continued)

*Primary Examiner* — Thomas A Giuliani
(74) *Attorney, Agent, or Firm* — Pauly, DeVries Smith & Deffner LLC

(57) ABSTRACT

A system, ablation probe, and method is provided for treating tissue, e.g., tissue having tumors. The treatment system is configured to automatically deliver infusaid to tissue when needed and comprises an ablation probe having an ablative element and at least one perfusion exit port. The system further comprises an ablation source operably coupled to the ablative element, and a pump assembly operably coupled to the perfusion exit port(s). The pump assembly is configured for pumping infusaid out through the perfusion exit port(s), preferably during the ablation process. The system further comprises a feedback device configured for controlling the amount of infusaid displaced by the pump assembly based on a sensed tissue parameter, e.g., tissue temperature or tissue impedance.

13 Claims, 8 Drawing Sheets

Related U.S. Application Data continuation of application No. 10/740,692, filed on Dec. 18, 2003, now Pat. No. 7,347,859.

(51) Int. Cl.
*A61B 18/12* (2006.01)
*A61B 18/00* (2006.01)

(52) U.S. Cl.
CPC . *A61B 18/1477* (2013.01); *A61B 2018/00005* (2013.01); *A61B 2018/00035* (2013.01); *A61B 2018/00071* (2013.01); *A61B 2018/00577* (2013.01); *A61B 2018/00595* (2013.01); *A61B 2018/00702* (2013.01); *A61B 2018/00875* (2013.01); *A61B 2018/00916* (2013.01); *A61B 2018/00934* (2013.01); *A61B 2018/143* (2013.01); *A61B 2018/1425* (2013.01); *A61B 2018/1432* (2013.01); *A61B 2018/1472* (2013.01); *A61B 2018/1475* (2013.01); *A61B 2218/002* (2013.01)

(58) Field of Classification Search
CPC ........ A61B 18/1487; A61B 2018/1425; A61B 2018/1427; A61B 2018/143; A61B 2018/1472; A61B 2018/1475; A61B 2018/0091; A61B 2018/00916; A61B 2018/00934; A61B 2018/00005; A61B 2018/00029; A61B 2218/002
USPC ......... 606/20–23, 25, 26–29, 32, 41, 45, 46; 607/96, 98, 99, 104, 105, 113, 115, 116
See application file for complete search history.

(56) References Cited

U.S. PATENT DOCUMENTS

| | | | |
|---|---|---|---|
| 5,334,193 A | | 8/1994 | Nardella |
| 5,517,008 A | * | 5/1996 | Francart, Jr. ............ G06M 1/00 235/91 F |
| 5,697,927 A | * | 12/1997 | Imran ................ A61B 18/1492 606/41 |
| 5,725,128 A | * | 3/1998 | Foster ................ B05B 11/3001 222/153.13 |
| 5,792,140 A | | 8/1998 | Tu et al. |
| 5,807,395 A | | 9/1998 | Mulier et al. |
| 6,017,338 A | | 1/2000 | Brucker et al. |
| 6,210,406 B1 | | 4/2001 | Webster et al. |
| 6,235,022 B1 | | 5/2001 | Hallock et al. |
| 6,352,539 B1 | * | 3/2002 | Avellanet .................. A61F 2/86 606/113 |
| 6,379,353 B1 | | 4/2002 | Nichols et al. |
| 6,409,722 B1 | | 6/2002 | Christopherson et al. |
| 6,607,524 B1 | | 8/2003 | LaBudde et al. |
| 6,613,047 B2 | | 9/2003 | Edwards et al. |
| 6,702,810 B2 | | 3/2004 | McClurken et al. |
| 6,743,015 B2 | | 6/2004 | Magnani et al. |
| 6,814,731 B2 | | 11/2004 | Swanson et al. |
| 7,025,768 B2 | * | 4/2006 | Elliott .............. A61B 17/12036 606/41 |
| 7,166,105 B2 | | 1/2007 | Mulier et al. |
| 7,282,051 B2 | * | 10/2007 | Rioux ................ A61B 18/1477 606/41 |
| 7,347,859 B2 | * | 3/2008 | Garabedian ........ A61B 18/0206 606/41 |
| 9,757,188 B2 | * | 9/2017 | Garabedian ........ A61B 18/0206 |
| 2003/0212394 A1 | * | 11/2003 | Pearson ............. A61B 18/1477 606/41 |
| 2004/0016427 A1 | * | 1/2004 | Byron .................. A61M 11/041 128/200.14 |
| 2004/0181214 A1 | * | 9/2004 | Garabedian ........ A61B 18/1477 606/41 |
| 2004/0220562 A1 | * | 11/2004 | Garabedian ............ A61B 18/14 606/41 |
| 2004/0225286 A1 | | 11/2004 | Elliott et al. |
| 2005/0137659 A1 | | 6/2005 | Garabedian et al. |
| 2005/0171526 A1 | | 8/2005 | Rioux et al. |
| 2008/0071266 A1 | * | 3/2008 | Rioux ................ A61B 18/1477 606/41 |
| 2008/0221562 A1 | | 9/2008 | Garabedian et al. |

FOREIGN PATENT DOCUMENTS

| | | |
|---|---|---|
| EP | 0608609 | 8/1994 |
| WO | 2005065561 | 7/2005 |

OTHER PUBLICATIONS

"File History," for U.S. Appl. No. 12/037,882.
"International Preliminary Report on Patentability," for PCT Application No. PCT/US2004/039804 dated Jun. 20, 2006 (7 pages).
"International Search Report and Written Opinion," for PCT Application No. PCT/US2004/039804 dated Mar. 22, 2005 (8 pages).
Livraghi, Tito et al., "Saline-Enhanced Radio-Frequency Tissue Ablation in the Treatment of Liver Metastases," Radiology, Jan. 1997, 205-210 (6 pages).

\* cited by examiner

TISSUE TREATMENT SYSTEM AND METHOD FOR TISSUE PERFUSION USING FEEDBACK CONTROL

RELATED APPLICATIONS

This application is a continuation of, and claims the benefit of and priority to, U.S. application Ser. No. 12/037,882, filed on Feb. 26, 2008, now U.S. Pat. No. 9,757,188, which claims the benefit of and priority to U.S. application Ser. No. 10/740,692, now U.S. Pat. No. 7,347,859, filed on Dec. 18, 2003, the disclosure of each of which are incorporated in their entirety for all purposes.

FIELD OF INVENTION

The invention(s) herein relate generally to the structure and use of radio frequency (RF) electrosurgical probes for the treatment of tissue.

BACKGROUND

The delivery of radio frequency (RF) energy to target regions within solid tissue is known for a variety of purposes of particular interest to the present invention(s). In one particular application, RF energy may be delivered to diseased regions (e.g., tumors) for the purpose of ablating predictable volumes of tissue with minimal patient trauma. RF ablation of tumors is currently performed using one of two core technologies.

The first technology uses a single needle electrode, which when attached to a RF generator, emits RF energy from the exposed, non-insulated portion of the electrode. This energy translates into ion agitation, which is converted into heat and induces cellular death via coagulation necrosis. The second technology utilizes multiple needle electrodes, which have been designed for the treatment and necrosis of tumors in the liver and other solid tissues. In general, a multiple electrode array creates a larger lesion than that created by a single needle electrode.

In theory, RF ablation can be used to sculpt precisely the volume of necrosis to match the extent of the tumor. By varying the power output and the type of electrical waveform, it is possible to control the extent of heating, and thus, the resulting ablation. However, the size of tissue coagulation created from a single electrode, and to a lesser extent a multiple electrode array, has been limited by heat dispersion. As a result, multiple probe insertions must typically be performed in order to ablate the entire tumor. This process considerably increases treatment duration and patent discomfort and requires significant skill for meticulous precision of probe placement. In response to this, the marketplace has attempted to create larger lesions with a single probe insertion. Increasing generator output, however, has been generally unsuccessful for increasing lesion diameter, because an increased wattage is associated with a local increase of temperature to more than 100° C., which induces tissue vaporization and charring. This then increases local tissue impedance, limiting RF deposition, and therefore heat diffusion and associated coagulation necrosis. In addition, patient tolerance appears to be at the maximum using currently available 200 W generators.

It has been shown that the introduction of saline into targeted tissue increases the tissue conductivity, thereby creating a larger lesion size. This can be accomplished by injecting the saline into the targeted tissue with a separate syringe. This injection can take place prior to or during the ablation process. See, e.g., Goldberg et al., Saline-Enhanced Radio-Frequency Tissue Ablation in the Treatment of Liver Metastases, Radiology, January 1997, pages 205-210. It has also been shown that, during an ablation procedure, the ablation probe, itself, can be used to perfuse saline (whether actively cooled or not) in order to reduce the local temperature of the tissue, thereby minimizing tissue vaporization and charring. For example, some probes may allow a physician, either before or during the ablation process, to manually inject a specific amount of fluid through the probe, which perfuses out of the needle electrode. These manually performed perfusion processes, however, are imprecise in that the optimum amount of perfusion is difficult to achieve. These perfusion processes also either demand additional attention from the physician performing the ablation procedure or require additional personnel to ensure that enough saline is perfused into the tissue.

One probe, which uses a multiple needle electrode array, can be connected to an injection pump network comprised of several syringes connected in parallel. The syringes are designed to automatically deliver the fluid through the probe and out of the respective needle electrodes, presumably at a prescribed time during the ablation process. While this automated perfusion process does not demand additional attention from the physician, it is imprecise and does not provide dynamic control over the amount of saline perfused into the target tissue, as well as the timing of the saline perfusion.

In addition, when needle electrodes are used to perfuse saline into the target tissue, whether performed manually or automatically, the perfusion exit ports within the needle electrodes often clog as the needle electrodes are introduced through the tissue. As a result, perfusion of the saline is hindered, and thus, the amount of saline perfused into the tissue may be insufficient. Even if the perfusion exit ports within the needle electrode(s) are not clogged, the amount of saline delivered through the needle electrode(s) may be insufficient due to an insufficient number or size of the perfusion exit ports. Also, in the automated perfusion process, additional time and skill is required to set up and connect the pump assembly to the ablation probe, thereby increasing the complexity of the ablation procedure.

SUMMARY OF THE INVENTION

In accordance with one aspect of the invention(s), a tissue treatment system is provided, which comprises an ablation probe. In one embodiment, the ablation probe is rigid, so that it can be percutaneously or laparoscopically introduced into a patient's body. Alternatively, the ablation probe can be flexible, e.g., if the ablation probe takes the form of an intravascular or extravascular catheter. The ablation probe further comprises an ablative element. Although many types of ablative elements are contemplated, the ablative element preferably takes the form of electrode(s), e.g., a single needle electrode or an array of needle electrodes. The ablation probe further comprises at least one perfusion exit port, which can be used to perfuse an infusaid into the surrounding tissue.

The system further comprises an ablation source operably coupled to the ablative element. If the ablative element is an electrode, the ablation source can be a RF generator. The system further comprises a pump assembly operably coupled to the perfusion exit port(s). The pump assembly can be external to the ablation probe or can be carried by the ablation probe. In one embodiment, the system comprises a source of infusaid, in which case, the pump assembly is configured for pumping the infusaid from the infusaid source out through the perfusion exit port(s).

The system further comprises a feedback device configured for controlling the amount of infusaid displaced by the pump assembly based on a sensed tissue parameter, e.g., tissue temperature or tissue impedance. In one embodiment, the feedback device comprises a sensor configured for sensing the tissue parameter, and a perfusion controller coupled to the sensor and the pump assembly. The perfusion controller is configured for controlling the pump assembly based on the sensed tissue parameter. In another embodiment, the feedback device comprises a perfusion valve associated with the distal end of the shaft. In this case, the perfusion valve forms the perfusion exit port, wherein the perfusion valve changes the size of the perfusion exit port based on the sensed tissue parameter. Thus, it can be appreciated that the treatment system automatically delivers infusaid to the tissue when needed.

In accordance with another aspect of the invention(s), a method of treating tissue is provided. The method comprises ablating the tissue (e.g., using radio frequency energy), sensing a tissue parameter (e.g., tissue temperature and/or tissue impedance), and perfusing the tissue with an infusaid based on the sensed tissue parameter. The tissue can be perfusing at anytime relative to the ablation process, but in a preferred method, the tissue is perfused during the tissue ablation. If the sensed tissue parameter is tissue temperature, the tissue perfusion may be commenced when the sensed temperature surpasses a first temperature, and ceased when the sensed temperature drops below a second temperature threshold. In a similar manner, if the sensed tissue parameter is tissue impedance, the tissue perfusion may be commenced when the sensed impedance surpasses a first impedance threshold, and ceased when the sensed impedance drops below a second impedance threshold.

In accordance with an aspect of the invention(s), an ablation probe comprises an elongate shaft having a distal end, and an ablative element disposed on the distal end of the shaft. In one embodiment, the ablation probe is rigid, so that it can be percutaneously or laparoscopically introduced into a patient's body. Alternatively, the ablation probe can be flexible, e.g., if the ablation probe takes the form of an intravascular or extravascular catheter. Although many types of ablative elements are contemplated, the ablative element preferably takes the form of electrode(s), e.g., a single needle electrode or an array of needle electrodes. The ablation probe further comprises at least one perfusion exit port, which can be used to perfuse an infusaid into the surrounding tissue. The ablation probe further comprises a perfusion lumen longitudinally extending within the shaft, and a perfusion control valve associated with the distal end of the shaft. The perfusion control valve has a port, the size of which changes with temperature. In one embodiment, the perfusion control valve comprises a reed valve having at least one reed, e.g., a pair of opposing reeds, or even four reeds. The reeds are configured change shape in order to control the size of the port. For example, each reed can comprise a bi-metallic flange or a nitinol flange that bends in the presence of a temperature change.

In accordance with an aspect of the invention(s), an ablation probe comprises an elongated shaft, which is preferably sufficiently rigid for percutaneous or laparoscopic introduction into a patient's body. Alternatively, the probe shaft can be flexible, e.g., if the ablation probe takes the form of an intravascular or extravascular catheter. The ablation probe further comprises an ablative element. Although many types of ablative elements are contemplated by the present invention(s), the ablative element preferably takes the form of electrode(s), e.g., a single needle electrode or an array of needle electrodes.

The ablation probe further comprises a perfusion lumen that extends through the probe shaft, and at least one perfusion exit port in fluid communication with the perfusion lumen. The perfusion lumen can be used to deliver an infusaid to the perfusion exit port(s) for perfusion of the surrounding tissue. The perfusion exit port(s) can be configured in any manner, but in one embodiment, side ports are provided. The perfusion exit port(s) can also be carried by the ablative element. The ablation probe further comprises a wicking material, e.g., cotton or fabric, disposed in the perfusion lumen. In this manner, the infusaid that travels through the perfusion lumen can be controlled without regard to the size of the perfusion exit port(s). The wicking material preferably is disposed within the entire length of the perfusion lumen to provide maximum control, but may also be disposed in only a portion of the perfusion lumen, depending on the amount of control required.

In accordance with another aspect of the present invention, a tissue treatment system comprises an ablation probe including an elongate shaft having a distal end, an ablative element disposed on the distal end of the shaft, a perfusion lumen longitudinally extending within the shaft, at least one perfusion exit port in fluid communication with the perfusion lumen, and a wicking material disposed in the perfusion lumen. The detailed features of the ablation probe can be similar to ablation probe described above. The system further comprises an ablation source operably coupled to the ablative element. If the ablative element is an electrode, the ablation source can be a RF generator. The system further comprises a pump assembly configured for pumping infusaid from the infusaid source through the perfusion lumen. The pump assembly can be external to the ablation probe or can be carried by the ablation probe. In one embodiment, the system comprises a source of infusaid, in which case, the pump assembly is configured for pumping the infusaid from the infusaid source out through the perfusion exit port(s).

In accordance with an aspect of the invention(s), an ablation probe comprises an elongated shaft, which is sufficiently rigid for percutaneous or laparoscopic introduction into a patient's body. Alternatively, the probe shaft can be flexible, e.g., if the ablation probe takes the form of an intravascular or extravascular catheter. The ablation probe further comprises an ablative element. Although many types of ablative elements are contemplated, the ablative element preferably takes the form of electrode(s), e.g., a single needle electrode or an array of needle electrodes.

The ablation probe further comprises a perfusion lumen that extends through the probe shaft, and at least one perfusion exit port in fluid communication with the perfusion lumen. The perfusion lumen can be used to deliver an infusaid to the perfusion exit port(s) for perfusion of the surrounding tissue. The perfusion exit port(s) can be configured in any manner, but in one embodiment, side ports are provided. The perfusion exit port(s) can also be carried by the ablative element.

The ablation probe further comprises a pump assembly carried by the proximal end of the shaft. The pump assembly is configured for pumping infusaid through the perfusion lumen and out the perfusion exit port(s). In one embodiment, the pump assembly comprises a reservoir for storing the infusaid, and a perfusion inlet port configured for transferring infusaid from an external source into the reservoir. In this case, the ablation probe further comprises a one-way check valve between the perfusion inlet port and the reservoir, wherein the check valve is configured for preventing the infusaid from being conveyed from the reservoir back through the perfusion inlet port. The ablation probe may further comprise another one-way check valve between the perfusion lumen and the reservoir, wherein the other check valve is configured for preventing the infusaid from being conveyed from the perfusion lumen back into the reservoir.

The pump assembly can be variously configured. In one embodiment, the pump assembly comprises a diaphragm adjacent the reservoir. In this case, the diaphragm has pumping stroke that displaces the infusaid from the reservoir into the perfusion lumen, and a return stroke that displaces infusaid from an external source into the reservoir. The diaphragm can have an active component, such as a piezo-electric element, configured for vibrating the diaphragm between pumping and return strokes. In another embodiment, the pump assembly comprises an elastomeric diaphragm adjacent the reservoir, wherein the diaphragm is configured for expanding to pressurize the reservoir in response to the conveyance of infusaid into the reservoir. In still another embodiment, the pump assembly comprises a plunger disposed in the reservoir and a spring configured to urge the plunger within the reservoir in one direction to pressurize the reservoir. The plunger may further be configured to be displaced in another direction, e.g., by manually pulling the plunger, to displace infusaid from an external source into the reservoir.

BRIEF DESCRIPTION OF THE DRAWINGS

The drawings illustrate the design and utility of embodiments of the invention, in which similar elements are referred to by common reference numerals, and in which.

DETAILED DESCRIPTION OF THE ILLUSTRATED EMBODIMENTS

Figure 1:
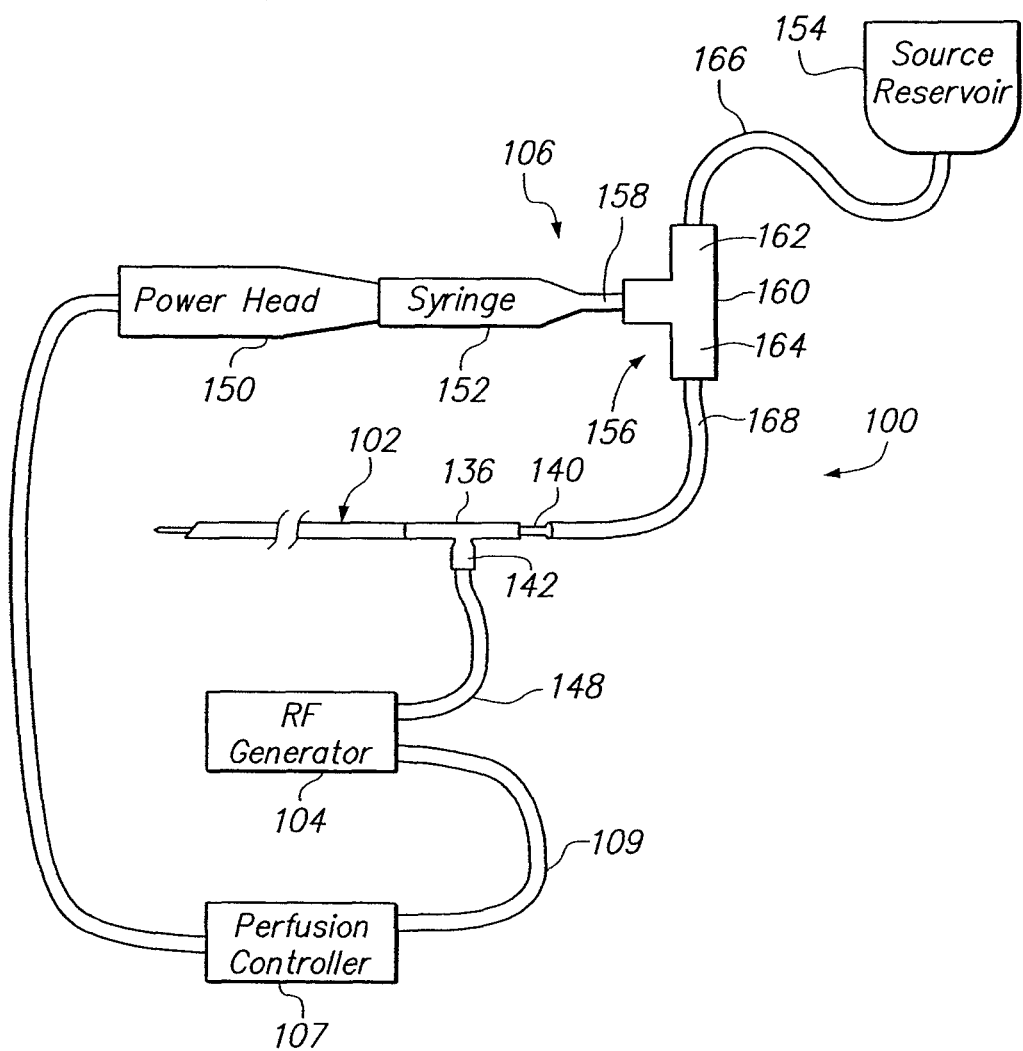
FIG. 1 is a plan view of a tissue treatment system constructed in accordance with one embodiment of the invention(s)

FIG. 1 illustrates a tissue treatment system 100 constructed in accordance with an exemplary embodiment of the invention(s). The tissue treatment system 100 generally comprises: a probe assembly 102 configured for introduction into the body of a patient for ablative treatment of target tissue; a radio frequency (RF) generator 104 configured for supplying RF energy to the probe assembly 102 in a controlled manner; a pump assembly 106 configured for perfusing an infusaid, such as saline, out through the probe assembly 102, so that a more efficient and effective ablation treatment is effected; and a perfusion controller 107 configured for controlling the amount and/or timing of the infusaid perfused out of the probe assembly 102.

Figure 2:
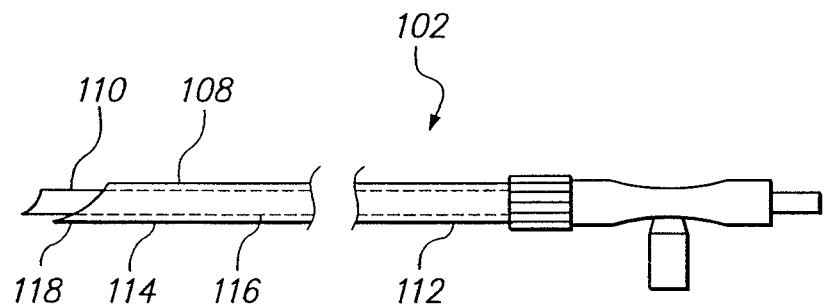
FIG. 2 is a side view of a probe assembly used in the tissue treatment system of FIG. 1.

Referring specifically now to FIG. 2, the probe assembly 102 generally comprises an ablation probe 110 and a cannula 108 through which the ablation probe 110 can be introduced. As will be described in further detail below, the cannula 108 serves to deliver the active portion of the ablation probe 110 to the target tissue. The cannula 108 has a proximal end 112, a distal end 114, and a perfusion lumen 116 (shown in phantom) extending through the cannula 108 between the proximal end 112 and the distal end 114. An open tapered point 118 is formed at the distal end 114 of the cannula 108 in order to facilitate introduction of the cannula 108 through tissue. As will be described in further detail below, the cannula 108 may be rigid, semi-rigid, or flexible, depending upon the designed means for introducing the cannula 108 to the target tissue. The cannula 108 is composed of a suitable material, such as plastic, metal or the like, and has a suitable length, typically in the range from 5 cm to 30 cm, preferably from 10 cm to 20 cm. If composed of an electrically conductive material, the cannula 108 is preferably covered with an insulative material. The cannula 108 has an outside diameter consistent with its intended use, typically being from 1 mm to 5 mm, usually from 1.3 mm to 4 mm. The cannula 108 has an inner diameter in the range from 0.7 mm to 4 mm, preferably from 1 mm to 3.5 mm.

Figure 3:
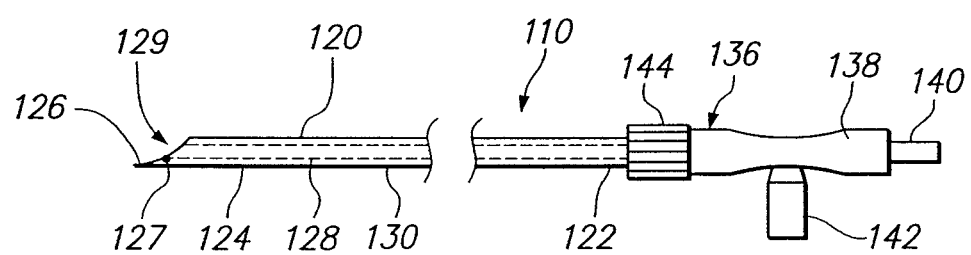
FIG. 3 is a side view of a single-needle electrode ablation probe used in the probe assembly of FIG. 2.

Referring further to FIG. 3, the ablation probe 110 generally comprises a shaft 120 having a proximal end 122 and a distal end 124, a single tissue penetrating needle electrode 126 formed at the end of the distal shaft end 124, and a perfusion lumen 128 (shown in phantom) longitudinally extending through the length of the probe shaft 120. The probe shaft 120 comprises a wall 130 that is preferably composed of an electrically conductive material, such as stainless steel, nickel-titanium alloy, nickel-chromium alloy, spring steel alloy, and the like. The needle electrode 126 is designed to penetrate into tissue as it is advanced to the target tissue site. Like the probe shaft 120, the needle electrode 126 is composed of an electrically conductive material, such as stainless steel, nickel-titanium alloy, nickel-chromium alloy, spring steel alloy, and the like. In fact, the needle electrode 126 is preferably formed as a unibody structure with the probe shaft 120.

In the illustrated embodiment, the needle electrode 126 has an open-ended tapered tip similar to the tip 118 of the cannula 108. The open end is in fluid communication with the perfusion lumen 128, thereby providing a perfusion exit port 129 from which infusaid is delivered to the tissue. Alternatively or optionally, side ports (not shown) can be provided in the probe shaft 120 in fluid communication with the perfusion lumen 128. Alternatively, the probe shaft 120 and/or the needle electrode 126 can have a porous structure that allows infusaid to exit out through the pores. Further details regarding the manufacture and functionality of porous structures in ablation probes are disclosed in application Ser. No. 10/740,692 filed Dec. 18, 2003, now U.S. Pat. No. 7,347,859, and which is expressly incorporated herein by reference. When using side ports or porous structures, the needle electrode 126 can have a closed-ended point, thereby facilitating introduction of the needle electrode 126 through the tissue along a straight line.

The ablation probe 110 further comprises a temperature sensor 127, such as a thermistor or thermocouple, mounted in the needle electrode 126. Signal wires (not shown) proximally extend from the temperature sensor 127 back through the probe shaft 120. The temperature sensor 127 is designed to measure the temperature of the tissue at any given time, thereby providing an indication of whether or not infusaid should be perfused into the tissue. That is, if the tissue temperature is relatively high, there is a danger that tissue charring may be occurring, resulting in premature increasing of local tissue impedance. At this point, the conductivity of the tissue should be increased by initiating or increasing perfusion of the infusaid into the tissue, thereby reducing the potential for tissue charring and premature impedance increase. If, on the other hand, the tissue temperature is relatively low, there is no danger of charring the tissue, in which case, tissue perfusion is not immediately needed. Continuous perfusion of infusaid, however, would create a danger that the tissue will become flooded with the infusaid, thereby reducing predictability of the ablation. As a practical example, the tissue temperature will drop between ablations when the tissue is not being actively ablated, in which case, continual perfusion is not desired. At this point, perfusion of the infusaid should be decreased or stopped.

Alternatively or optionally, an impedance sensor may be used to measure the impedance of the tissue at any given time. Preferably, the needle electrode 126 acts as the impedance sensor, which will complete an electrical circuit with an external grounding electrode in order to provide measurements of the tissue impedance. In a similar manner as tissue temperature, tissue impedance provides an indication of whether or not infusaid should be perfused into the tissue. That is, a relatively high tissue impedance indicates that the tissue may be charring, at which point perfusion of infusaid is desired. A relatively low impedance indicates that there is no danger of tissue charring, at which point perfusion of infusaid is not desired.

Referring back to FIG. 3, the ablation probe 110 further comprises a connector assembly 136 mounted on the proximal shaft end 122. The connector assembly 136 comprises a housing 138, a perfusion inlet port 140, such as a male luer connector, mounted to the proximal end of the housing 138, and a RF/signal port 142 mounted to the side of the housing 138. The perfusion inlet port 140 is in fluid communication with the perfusion lumen 128 of the probe shaft 120 via an internal conduit (not shown) within the housing 138, and the RF/signal port 142 is in electrical communication with the needle electrode 126 via the probe shaft wall 130, which extends into the housing 138. The RF/signal port 142 is also in electrical communication with the temperature sensor 127 (or alternatively an impedance sensor) via signal wires (not shown) extending through the probe shaft 120. The connector assembly 136 is also provided with a nut 144, which engages the threads (not shown) of the cannula 108 in order to integrate the probe assembly 102 once the needle electrode 126 is properly located at the target ablation site. The connector assembly 136 can be composed of any suitable rigid material, such as, e.g., metal, plastic, or the like.

Figure 4:
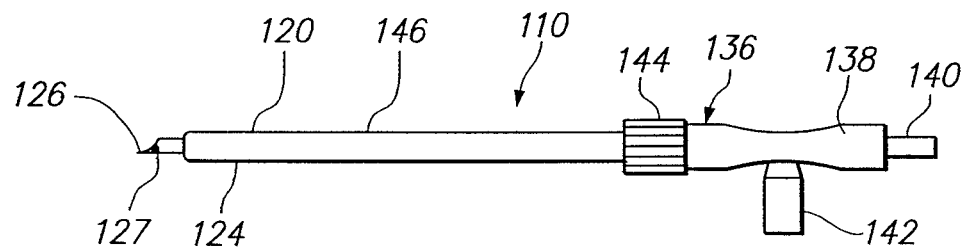
FIG. 4 is a side view of an alternatively single-needle electrode ablation probe that can be used in the probe assembly of FIG. 2.

If the cannula 108 is not used, or if the cannula 108 is composed of an electrically conductive material, the ablation probe 110 may comprise an optional insulative sleeve 146 (illustrated in FIG. 4) that is disposed around the entire length of the probe shaft 120, leaving the needle electrode 126 exposed. The sleeve 146 can be formed around the probe shaft 120 in any one of a variety of manners, e.g., by co-extruding it over the probe shaft 120. If the cannula 108 is not used, or if the cannula 108 is composed of an electrically conductive material, the sleeve 146 is preferably composed of an electrically insulative material, such as plastic. In this manner, the RF energy conveyed through the probe shaft 120 will be concentrated at the target ablation site adjacent the needle electrode 126.

Referring back to FIG. 1, the RF generator 104 is electrically connected to the RF port 142 of the connector assembly 136 via an RF/signal cable 148, which as previously described, is indirectly electrically coupled to the needle electrode 126 through the probe shaft 120, and indirectly coupled to the temperature sensor 127 (or the impedance sensing element) via signal wires. The RF generator 104 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for tissue ablation. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100 W) and RF3000™ (200 W).

RF current is preferably delivered from the RF generator 104 to the needle electrode 126 in a monopolar fashion, which means that current will pass from the needle electrode 126, which is configured to concentrate the energy flux in order to have an injurious effect on the surrounding tissue, and a dispersive electrode (not shown), which is located remotely from the needle electrode 126 and has a sufficiently large area (typically 130 $cm^2$ for an adult), so that the current density is low and non-injurious to surrounding tissue. In the illustrated embodiment, the dispersive electrode may be attached externally to the patient, e.g., using a contact pad placed on the patient's flank. If the needle electrode 126 is used as an impedance sensor, the dispersive electrode will be used to connect the circuit from the tissue back to the RF generator 104.

The pump assembly 106 comprises a power head 150 and a syringe 152 that is front-loaded on the power head 150 and is of a suitable size, e.g., 200 ml. The power head 150 and the syringe 152 are conventional and can be of the type described in U.S. Pat. No. 5,279,569 and supplied by Liebel-Flarsheim Company of Cincinnati, Ohio. The pump assembly 106 further comprises a source reservoir 154 for supplying the infusaid to the syringe 152. The infusaid can be optionally cooled to provide the additional beneficial effect of cooling the needle electrode 126 and the surrounding tissue during the ablation process. The pump assembly 106 further comprises a tube set 156 removably secured to an outlet 158 of the syringe 152. Specifically, a dual check valve 160 is provided with first and second legs 162 and 164, of which the first leg 162 serves as a liquid inlet connected by tubing 166 to the source reservoir 154. The second leg 164 is an outlet leg and is connected by tubing 168 to the perfusion inlet port 140 on the connector assembly 136.

Thus, it can be appreciated that the pump assembly 106 can be operated to periodically fill the syringe 152 with the infusaid from the source reservoir 154 via the tubing 166, and convey the infusaid from the syringe 152, through the tubing 168, and into the perfusion inlet port 140 on the connector assembly 136. The infusaid is then conveyed through the perfusion lumen 128 of the probe shaft 120, and out through the needle electrode 126.

Other types of pump assemblies are also available for pumping infusaid through the probe shaft 120. For example, a saline bag can simply be connected to the perfusion inlet port 140 on the connector assembly 136 via tubing, and then raised above the patient a sufficient height to provide the head pressure necessary to convey the infusaid through the probe shaft 120 and out of the needle electrode 126. Alternatively, pump assemblies can be conveniently incorporated within the connector assembly 136, as described in further detail below.

The perfusion controller 107 is functionally coupled between the power head 150 of the pump assembly 106 and the temperature sensor 127. In the illustrated embodiment, the perfusion controller 107 is a stand-alone device that is coupled to the temperature sensor 127 through the RF generator 104 via a cable 109. Specifically, the perfusion controller 107 is coupled to the RF generator 104 to obtain temperature feedback signals from the temperature sensor 127. Alternatively, the perfusion controller 107 can be incorporated into the RF generator 104, in which case, the cable 109 is not required. The perfusion controller 107 can also be incorporated into the pump assembly 106. The RF generator 104, pump assembly 106, and perfusion controller 107 can even be incorporated into a single device similar to that disclosed in U.S. Pat. No. 6,235,022, which is hereby fully and expressly incorporated herein by reference. A commercial embodiment of such an assembly (absent the perfusion feedback aspects) is marketed as the Model 8004 RF generator and Pump System by Boston Scientific Corporation, located in San Jose, Calif. The Model 8004 RF generator need only be modified to incorporate the perfusion controller 107 described herein.

In any event, the perfusion controller 107 turns the power head 150 on when the tissue temperature, as indicated by the temperature feedback signals received from the temperature sensor 127, surpasses an upper temperature threshold. As a result, the power head 150 will operate the syringe 152 in order to perfuse the infusaid through the tubing assembly 156 and into the perfusion inlet port 140 of the ablation probe 110. The infusaid then travels down the perfusion lumen 128 of the ablation probe 110, and out through the perfusion exit port 129 into the tissue. The conductivity of the tissue will then increase, thereby providing for a more efficient and effective ablation process. When the tissue temperature drops below a lower temperature threshold, indicating that there is too much infusaid within the tissue or the ablation process has temporarily or permanently ceases, the perfusion controller 107 will turn the power head 150 off, thereby preventing further perfusion of the infusaid until the tissue temperature surpasses the upper temperature threshold again.

The lower temperature threshold should be set at a level that is not so close to the upper threshold level that the power head 150 will be rapidly turned on and off during the ablation process, but should not be set so far from the upper threshold level that a wide tissue temperature variance is created. Alternatively, instead of using a lower temperature threshold, the perfusion controller 107 may turn the power head 150 on for a predetermined period of time, after which the power head 150 is turned off until the tissue temperature surpasses the upper temperature threshold.

In an alternative embodiment, the feedback control system can be overridden by providing a switch (not shown) on the pump assembly 106 that can be manually operated by a physician. In this case, the switch can be alternately operated to turn the power head 150 on and off at the discretion of the physician. For example, the physician may desire to perfuse infusaid within the tissue prior to initiating the ablation process, or otherwise desire to increase or reduce the amount of infusaid perfuse regardless of the nature of the temperature feedback signals.

Figure 5:
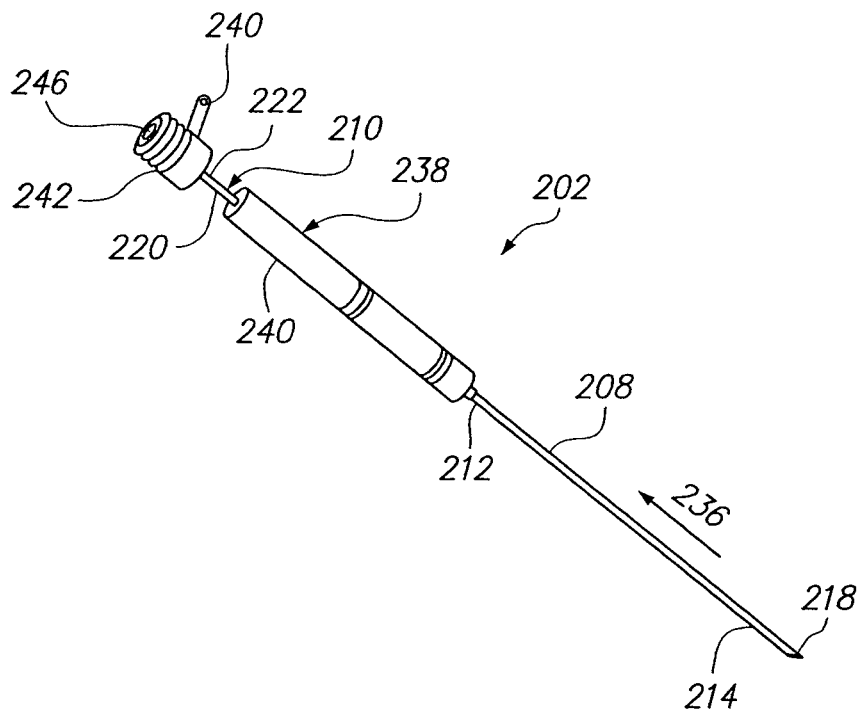
FIG. 5 is a perspective view of a multi-needle electrode probe assembly that can be used in the tissue treatment system of FIG. 1, wherein the probe assembly is in its retracted state.
Figure 6:
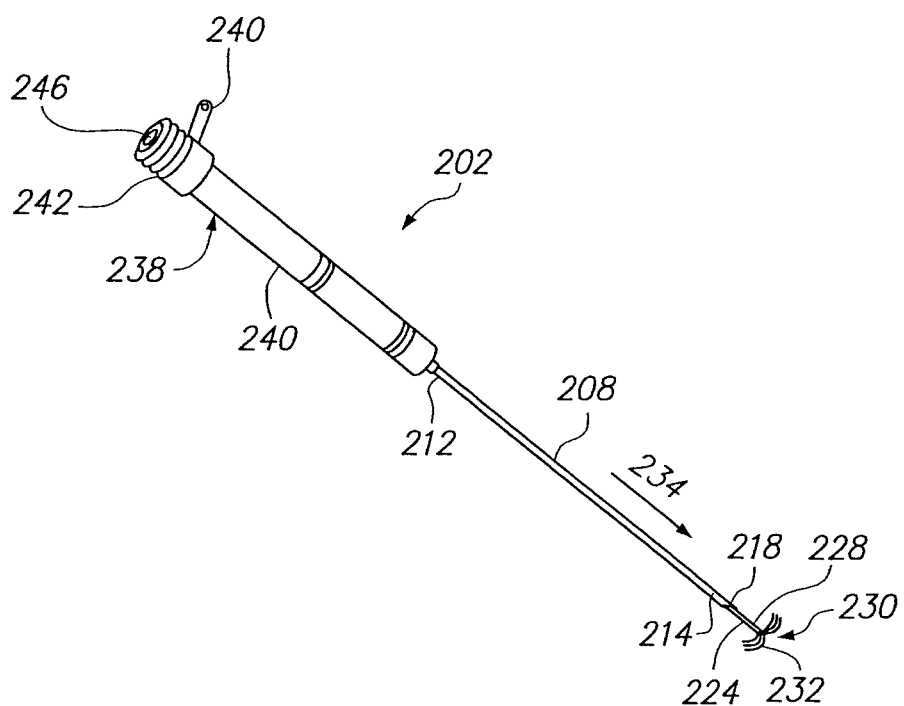
FIG. 6 is a perspective view of the probe assembly of FIG. 5, wherein the probe assembly is in its deployed state.

Referring now to FIGS. 5 and 6, an alternative embodiment of a probe assembly 202, which can be used in the tissue treatment system 100, will now be described. The probe assembly 202 generally comprises an elongated cannula 208 and an inner probe 210 slidably disposed within the cannula 208. The cannula 208 has a proximal end 212, a distal end 214, and a perfusion lumen (not shown) extending through the cannula 208 between the proximal end 212 and the distal end 214. An open tapered point 218 is formed at the distal end 214 of the cannula 208 in order to facilitate introduction of the cannula 208 through tissue. As with the cannula 108, the cannula 208 serves to deliver the active portion of the inner probe 210 to the target tissue, and may be rigid, semi-rigid, or flexible depending upon the designed means for introducing the cannula 108 to the target tissue. The cannula 208 may have the same material composition and dimensions as the cannula 108.

The inner probe 210 comprises a reciprocating shaft 220 having a proximal end 222 and a distal end 224 (shown in FIG. 5); a perfusion lumen (not shown) extending through the shaft 220 between the proximal end 222 and distal end 224; a cylindrical interface 228 mounted to the distal end 224 of the shaft 220; and an array 230 of tissue penetrating needle electrodes 232 mounted within the cylindrical interface 228. The shaft 220 is slidably disposed within the perfusion lumen of the cannula 208, such that longitudinal translation of the shaft 220 in a distal direction 234 deploys the electrode array 226 from the distal end 214 of the cannula 208 (FIG. 6), and longitudinal translation of the shaft 218 in a proximal direction 236 retracts the electrode array 226 into the distal end 214 of the cannula 108 (FIG. 5).

Preferably, each of the needle electrodes 232 (or a subset thereof) comprises a lumen (not shown) that terminates in a perfusion exit port (not shown) and that is in fluid communication with the perfusion lumen within the shaft 220. In this manner, each of the needle electrodes 232 is capable of perfusing the infusaid into the tissue. Alternatively, or optionally, the cylindrical interface 228 or the probe shaft 220, itself, can have a perfusion exit port. Thus, like the ablation probe 110, infusaid may flow through the perfusion lumen of the shaft 220, through the respective lumens of the needle electrodes 232 and out the exit ports. Alternatively, the needle electrodes 232 and/or the probe shaft 220 can have a porous structure.

Like the previously described probe 110, the probe 210 comprises a temperature sensor (not shown), which is mounted at the base of the needle electrodes 232, preferably adjacent the cylindrical interface 228. Alternatively, or optionally, the needle electrodes 232 can act as an impedance sensor. Signal wires (not shown) proximally extend from the temperature sensor (or needle electrodes 232 if used as impedance sensors) back through the probe shaft 220.

The probe assembly 202 further comprises a connector assembly 238, which includes a connector sleeve 240 mounted to the proximal end 212 of the cannula 208 and a connector member 242 slidably engaged with the sleeve 240 and mounted to the proximal end 222 of the shaft 220. The connector member 242 comprises a perfusion inlet port 240 and a RF/signal port 246 in which the proximal ends of the needle electrodes 230 (or alternatively, intermediate conductors) extending through the shaft 220 of the inner probe 210 are coupled. The signal wires from the temperature sensor 127 are also coupled to the RF/signal port 246. The connector assembly 238 can be composed of any suitable rigid material, such as, e.g., metal, plastic, or the like.

RF current can be delivered to the electrode array 230 in a monopolar fashion, as previously described above, or in a bipolar fashion, which means that current will pass between "positive" and "negative" electrodes 232 within the array 230. In a bipolar arrangement, the positive and negative needle electrodes 232 will be insulated from each other in any regions where they would or could be in contact with each other during the power delivery phase.

Further details regarding needle electrode array-type probe arrangements are disclosed in U.S. Pat. No. 6,379,353, which is hereby expressly incorporated herein by reference.

Having described the structure of the tissue treatment system 100, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 7A:
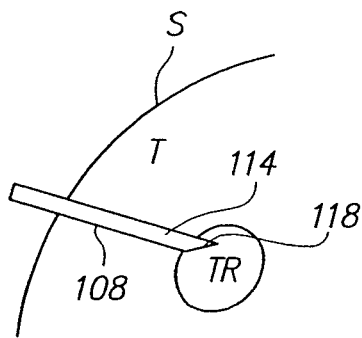
FIGS. 7A-7C illustrate cross-sectional views of one method of using the tissue treatment system of FIG. 1 to treat tissue.
Figure 7B:
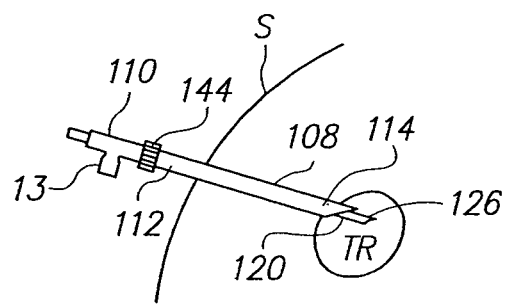
Figure 7C:
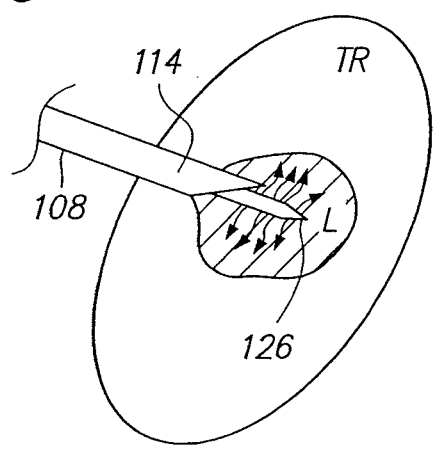

Referring now to FIGS. 7A-7C, the operation of the tissue treatment system 100 is described in treating a treatment region TR within tissue T located beneath the skin or an organ surface S of a patient. The probe assembly 102 is described in this operation, although the probe assembly 202 can be alternatively used. The cannula 108 is first introduced through the tissue T, so that the distal end 114 of the cannula 108 is located at the treatment region TR, as shown in FIG. 7A. This can be accomplished using any one of a variety of techniques. In a preferred method, the cannula 108 and probe 110 are introduced to the treatment region TR percutaneously directly through the patient's skin or through an open surgical incision. In this case, the sharpened tip 118 of the cannula 108 facilitates introduction to the treatment region TR. In such cases, it is desirable that the cannula 108 or needle be sufficiently rigid, i.e., have a sufficient column strength, so that it can be accurately advanced through tissue T. In other cases, the cannula 108 may be introduced using an internal stylet that is subsequently exchanged for the ablation probe 110. In this latter case, the cannula 108 can be relatively flexible, since the initial column strength will be provided by the stylet. More alternatively, a component or element may be provided for introducing the cannula 108 to the target ablation site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 108 and probe 110 can then be introduced through the sheath lumen, so that the distal end 114 of the cannula 108 advances from the sheath into the target ablation site TS.

After the cannula 108 is properly placed, the probe shaft 120 is distally advanced through the cannula 108 to deploy the needle electrode 126 out from the distal end 114 of the cannula 108, as shown in FIG. 7B. Once the cannula 108 and probe 110 are properly positioned, the ablation probe 110 and cannula 108 can then be integrated with each other by threading the nut 144 around the threaded portion of the cannula proximal end 112. The RF generator 104 is then connected to the connector assembly 136 via the RF port 142, and the pump assembly 106 is connected to the connector assembly 136 via the perfusion inlet port 140. The RF generator 104 is then operated to ablate the treatment region TR, and the pump assembly 106, under control of the perfusion controller 107, is operated to perfuse the treatment region TR with infusaid when necessary, i.e., when the tissue temperature is above the upper temperature threshold. As a result, lesion L will be created, as illustrated in FIG. 7C, which will eventually expand to include the entire treatment region TR.

Figure 8:
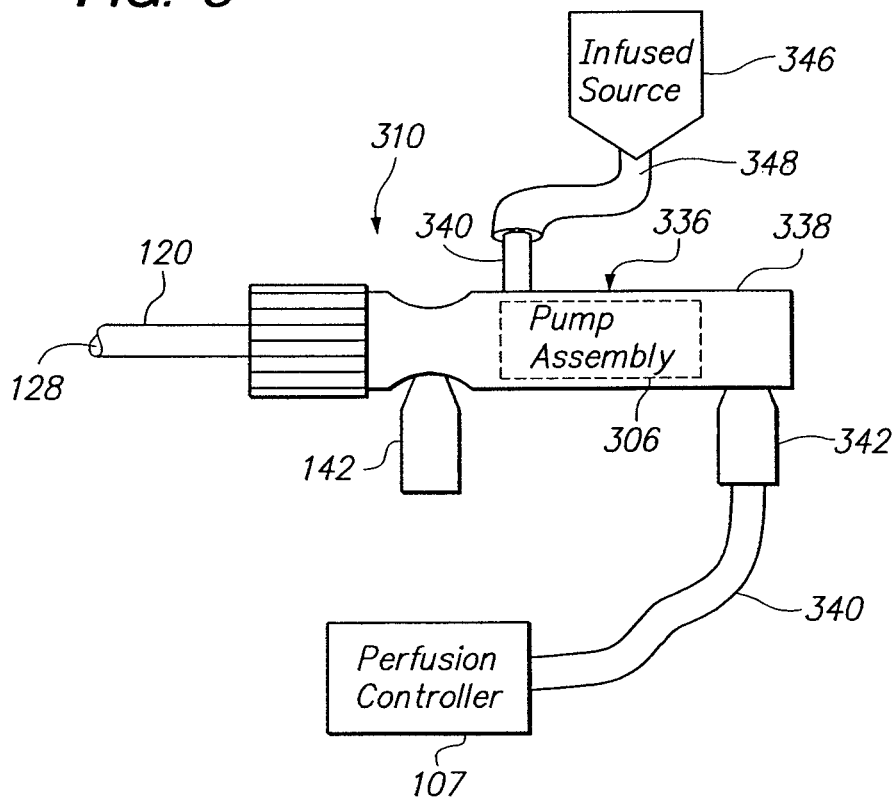
FIG. 8 is a side view of the proximal end of another ablation probe that carries a pump assembly for pumping infusaid through the ablation probe.

Although the pump assembly 106 has been described as being external to the ablation probe 110, a pump can alternatively be incorporated into an ablation probe. Such a feature obviates the need to set up and connect the pump assembly to the ablation probe, thereby simplifying the ablation process. Turning to FIG. 8, an ablation probe 310 with an incorporated pump will now be described. The ablation probe 310 is similar to the previously described ablation probe 110, with the exception that the ablation probe 310 includes a connector assembly 336 with a pump assembly 306. The connector assembly 336 comprises a housing 338 in which the pump assembly 306 is mounted.

The pump assembly 306 is powered and controlled by the perfusion controller 107, which can be either be located within the RF generator 104 or can be a stand-alone device. If room permits, the perfusion controller 107 can even be incorporated within the connector assembly 336—perhaps as another component of the pump assembly 306. The connector assembly 336 comprises a perfusion control port 342 mounted to the exterior of the housing 338. The perfusion controller 107 is electrically coupled to the pump assembly 306 via a power/signal cable 340, which mates with the perfusion control port 342. Alternatively, if the perfusion controller 107 is incorporated into the RF generator 104, the perfusion controller 107 can be connected to the pump assembly 306 via the RF/signal port 142, in which case, a separate cable 340 and perfusion control port 342 is not needed. Thus, the perfusion controller 107 may supply power to the pump assembly 306 and alternately turn the pump assembly 306 on and off by transmitting control signals to the pump assembly 306.

The connector assembly 336 further comprises a perfusion inlet port 340 mounted to the exterior of the housing 338. The perfusion inlet port 340 is in fluid communication with the pump assembly 306. A source of infusaid 346, such as a saline bag, is in fluid communication with the perfusion inlet port 340 via tubing 348. Thus, the pump assembly 306 can be operated to pump the infusaid supplied by the infusaid source 346 into the perfusion lumen 128 of the ablation probe 310.

Figure 9:
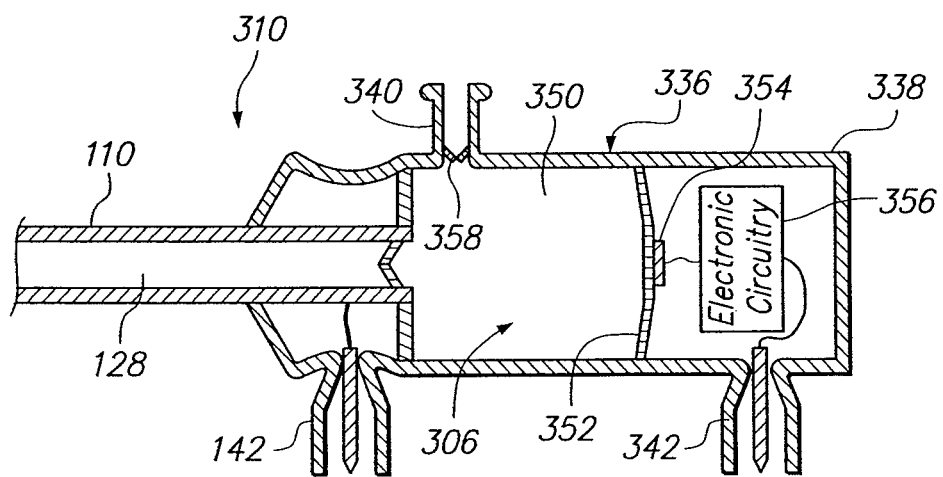
FIG. 9 is a cross-sectional view of the proximal end of the ablation probe of FIG. 8, particularly showing the use of a piezoelectric activated pump assembly.
Figure 10:
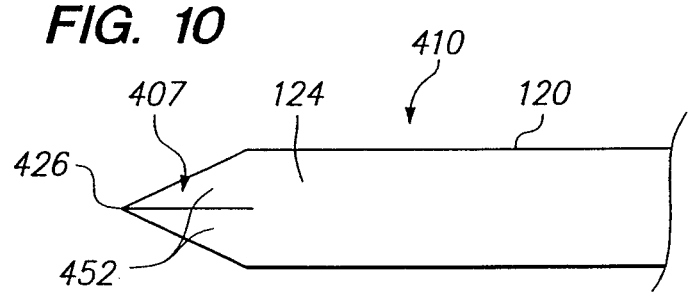
FIG. 10 is a side view of the distal end of still another single-needle electrode ablation probe that uses a perfusion control valve to regular the flow of infusaid through the ablation probe, particularly showing the perfusion control valve in a closed state.
Figure 11:
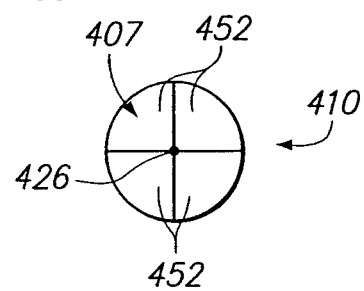
FIG. 11 is an axial view of the ablation probe illustrated in FIG. 10.

Turning now to FIG. 9, the pump assembly 306 will now be described in further detail. The pump assembly 306 comprises a reservoir 350 that stores the infusaid received from the infusaid source 346. In the illustrated embodiment, the active component of the pump assembly 306 is based on piezoelectric transducer technology. Specifically, the pump assembly 306 comprises a diaphragm 352 that encloses the proximal side of the reservoir 350. The diaphragm 352 is composed of an elastomeric material, e.g., a polymeric substance, such that the diaphragm 352 can alternatively move toward and away from the reservoir 350 in an elastic manner. The pump assembly 306 further comprises a piezoelectric element 354 suitably bonded to the proximal side of the diaphragm 352, and an electronic circuit 356 that is electrically coupled to electrodes (not shown) on the piezoelectric element 354. Under control of the perfusion controller 107, the electronic circuit 356 transmits electrical current to the piezoelectric element 354 at a high frequency, which causes the piezoelectric element 354 to vibrate towards (the pumping stroke) and away from (the return stroke) the infusaid stored in the reservoir 350.

Thus, during the pumping stroke, the diaphragm 352 moves into the reservoir 350, causing the pressure within the reservoir 350 to increase. As a result, a portion of the infusaid is displaced from the reservoir 350 into the perfusion lumen 128. A one-way check valve 358 is provided between the perfusion inlet port 140 and the reservoir 350 to prevent the infusaid in the reservoir 350 from being displaced back through the perfusion inlet port 140 and into the infusaid source 346. During the return stroke, the diaphragm 352 moves away from the reservoir 350, causing the pressure within the reservoir 350 to decrease. As a result, a portion of the infusaid within the infusaid source 346 is forced (sucked) into the reservoir 350. Another one-way check valve 360 is provided between the perfusion lumen 128 and the reservoir 350 to prevent the infusaid within the perfusion lumen 128 from being forced (sucked) back into the reservoir 350. Similar types of piezoelectric activated devices are marketed as fluid atomizers by APC International, Ltd., located in Mackeyville, Pa.

The pump assembly 306 can also be incorporated into a multi-electrode ablation probe similar to that illustrated in FIGS. 5 and 6. In this case, the pump assembly 306 may be incorporated into the connector member 242. The ablation probe 310 can be used with the cannula 108 and the RF generator 104 to ablate and perfuse tissue in the same manner described above with respect to FIGS. 7A-7C. The main difference is that an external pump assembly need not be set up and connected to the ablation probe 310. Rather, only the infusaid source 346 need only be connected to ablation probe 310.

Although the previously described perfusion controller 107 has been described as controlling the perfusion of the infusaid by controlling the operation of the pump assemblies 106 and 306, a perfusion controller, which takes the form of a valve, can instead be used to control the perfusion downstream from the pump assemblies 106 and 306. Specifically, and with reference to FIGS. 10-13, an ablation probe 410 that implements this concept will now be described. The ablation probe 410 is similar to the previously described ablation probes 110 and 310, with the exception that the distal end 124 of the probe shaft 120 comprises a perfusion control valve 407 that controls the amount of infusaid perfused into the tissue. The ablation probe 410 may operate with the RF generator 104 and the external pump assembly 106 illustrated in FIG. 1, or alternatively, the pump assembly 306 illustrated in FIGS. 8 and 9 can be incorporated into the proximal end of the ablation probe 410. Because direct control is exercised over the pump assembly, the ablation probe 410 may alternatively incorporate various types of manually activated pump assemblies within its proximal end, as will be described in further detail below.

Figure 12:
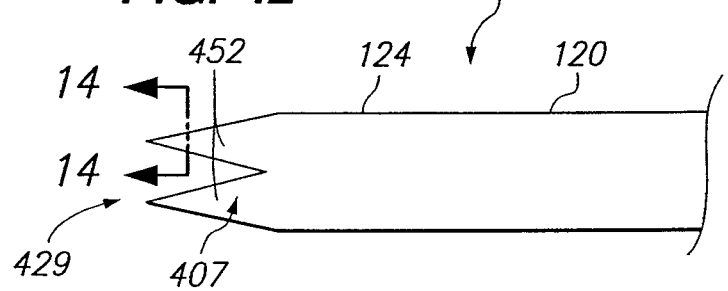
FIG. 12 is a side view of the distal end of the ablation probe of FIG. 10, wherein the perfusion control valve is particularly shown in an open state.
Figure 13:
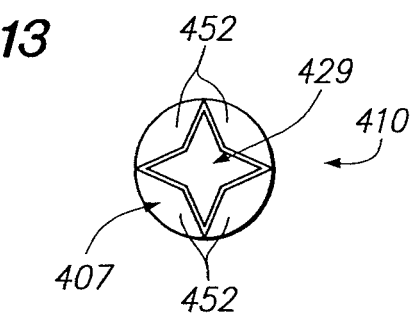
FIG. 13 is an axial view of the ablation probe illustrated in FIG. 12.

In the illustrated embodiment, the control valve 407 takes the form of a reed valve that comprises four reeds 452 and a perfusion exit port 429 (shown in FIGS. 12 and 13). The reeds 452 are designed to collapse upon each other in the presence of a relatively low tissue temperature (FIGS. 10 and 11), and move away from other in the presence of a relatively high temperature (FIGS. 12 and 13). When fully collapsed, the reeds 452 form a tissue penetrating point 426 that facilitates introduction of the ablation probe 410 through tissue. Notably, the control valve 407 will only be exposed to body temperature during its introduction through the tissue, and thus, the reeds 452 will be fully collapsed in order to form the point 426. During the ablation process, the control valve 407 will open, at which point the tissue penetrating tip 426 will not exist. Because the ablation probe 410 will presumably be stabilized during the ablation process, however, the tissue penetrating tip 426 is not needed.

Figure 14:
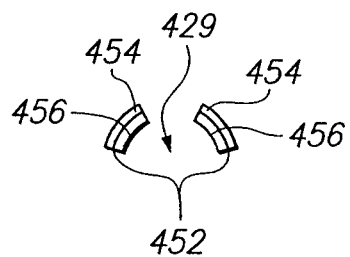
FIG. 14 is a cross-sectional view of two reeds used in the perfusion control valve illustrated in FIG. 12, taken along the lines 14-14.
Figure 15:
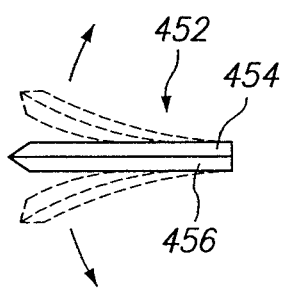
FIG. 15 is a side view of a reed used in the perfusion control valve of FIGS. 12 and 14, particularly showing the dynamic bending functionality of the reed in response to temperature changes.

Referring now to FIGS. 14 and 15, each of the reeds 452 is composed of a bi-metallic flange, so that the reeds 452 collapse towards each other and move away from either in the presence of temperature changes. That is, each reed 452 comprises an outer layer of metal 454 having a specific coefficient of thermal expansion (CTE) and an inner layer of metal 456 having a higher CTE. For example, the outer layer 454 can be composed of gold, which has a CTE of $7.9 \times 10^{-6}/°$ F. and the inner layer 456 can be composed of copper, which has a CTE of $9.2 \times 10^{-6}/°$ F.

Thus, when the tissue temperature increases, the inner layer 456 will expand along the length of the reed 452 at a rate that is greater than the rate that the outer layer 454 expands along the length of the reed 452. As a result, each reed 452 will deform outward, thereby increasing the size of the perfusion exit port 429, which, in turn, increases the amount of infusaid that is perfused out of the ablation probe 410. Each reed 452 will stop deforming outward until the temperature reaches a stead-state—preferably below 100° C. In contrast, when the tissue temperature decreases, the inner layer 456 will contract along the length of the reed 452 at a rate that is greater than the rate that the outer layer 454 contracts along the length of the reed 452. As a result, each reed 452 will deform inward, thereby decreasing the size of the perfusion exit port 429, which, in turn, decreases the amount of infusaid that is perfused out of the ablation probe 410. Each reed 452 will stop deforming inward until either the temperature reaches a stead-state or the reeds 452 have fully collapsed upon each other, whichever happens first. Preferably, the perfusion exit port 429 is completely closed when the reeds 452 are in the fully collapsed state, so that no infusaid can be perfused out of the ablation probe 410 at this point.

It should be noted that there are other ways in which the reeds 452 can deform in the presence of tissue temperature change. For example, the reeds 452 may be composed of nitinol, which is preferably shaped and processed, such that the reeds 452 deform outward when the tissue temperature increases, and curved inward when the tissue temperature decreases. The manufacture and functionality of nitinol flanges exhibiting these properties is well known in the art and will thus not be discussed in further detail. Thus, like a bi-metallic reed, when the temperature increases, each reed 452 will deform outward, which, in turn, increases the amount of infusaid that is perfused from the ablation probe 410. When the temperature decreases, each reed 452 will deform inward, which, in turn, decreases the amount of infusaid that is perfused from the ablation probe 410.

The ablation probe 410 further comprises an electrode, which can either be carried by, or integrated in, the reeds 452 of the control valve 407. For example, a conductive element (not shown) can be applied to each reed 452, with each conductive element forming a portion of the electrode, or the outer layer 454 of each reed 452 (in the case of a bi-metallic reed 452) can function as a portion of the electrode. The outside of the reeds 452 can optionally be faceted in order to facilitate visualization of the electrode during fluoroscopy.

Figure 16:
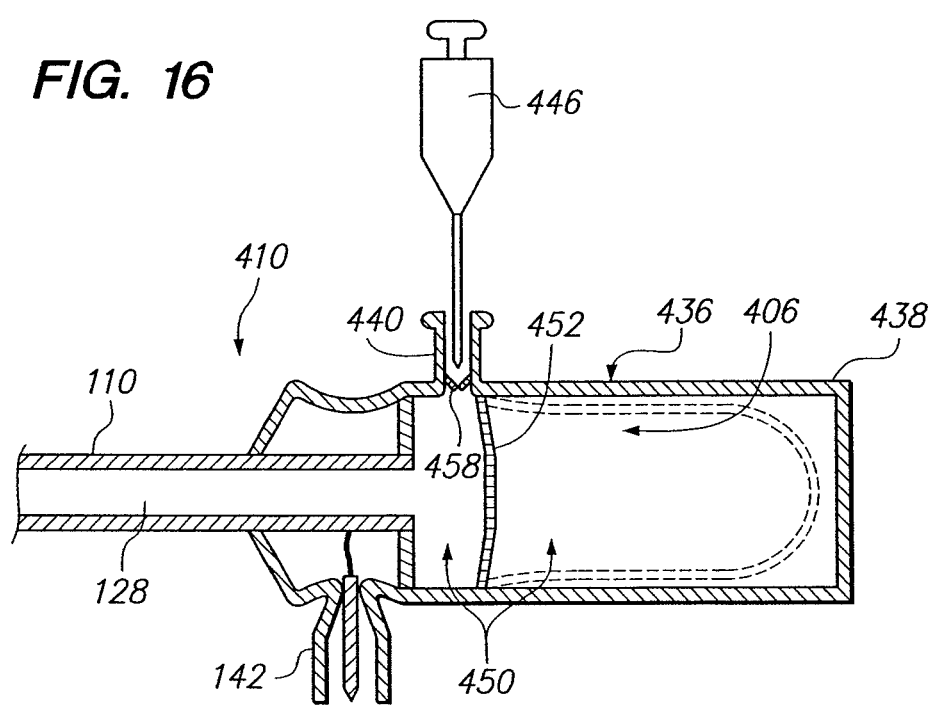
FIG. 16 is a cross-sectional view of the proximal end of still another ablation probe that uses an elastomeric diaphragm pump assembly to pump infusaid through the ablation probe.

As briefly discussed above, manually activated pump assemblies can alternatively be incorporated into the proximal end of the ablation probe 410. For example, FIG. 16 illustrates the proximal end of the ablation probe 410, which includes a connector assembly 436 that is similar to the previously described connector assembly 336, with the exception that it includes a manually activated pump assembly 406. The connector assembly 436 comprises a housing 438 in which the pump assembly 406 is mounted. The connector assembly 436 further comprises the previously described RF port 142 to which the RF generator 104 can be connected, and a perfusion inlet port 440 mounted to the exterior of the housing 438. The perfusion inlet port 440 is in fluid communication with the pump assembly 406. A source of infusaid 446, such as syringe, can be used to inject infusaid into the connector assembly 436 via the perfusion inlet port 440. Thus, the pump assembly 406 can be operated-to pump the infusaid supplied by the infusaid source 446 into the perfusion lumen 128 of the ablation probe 410.

In performing its function, the pump assembly 406 comprises a reservoir 450 that stores the infusaid received from the infusaid source 446, and a diaphragm 452 that encloses the proximal side of the reservoir 450. Thus, when the syringe 152 conveys infusaid through the perfusion inlet port 440 and into the reservoir 450 under positive pressure, the diaphragm 452 will expand from its fully contracted position towards the proximal end of the housing 438 in order to accommodate the infusaid reservoir 450, as shown in phantom in FIG. 16. Once the diaphragm 452 is forced against the proximal end of the connector housing 438, the reservoir 450 will be completely filled with infusaid, and the reservoir 450 will, in turn, be fully pressurized. A one-way check valve 458 is provided within the perfusion inlet port 440 to prevent the infusaid from escaping once the syringe 446 is removed from the perfusion inlet port 440. Alternatively, the syringe 446 can be left in place during the ablation process, in which case, a one-way check valve may not be needed.

Notably, the control valve 407 at the proximal end of the ablation probe 410 will be exposed to room temperature during the filling process, in which case, the perfusion exit port 429 will be totally closed at room temperature, thereby preventing infusaid from escaping the ablation probe 410 as the reservoir 450 is being filled. During the ablation process, the control valve 407 will be exposed to high temperatures, in which case, the perfusion exit port 429 will open, with the size of the opening depending upon the immediate tissue temperature. At this point, the infusaid, which is under positive pressure, will be forced out of the reservoir 450, through the perfusion lumen 128, and out of the perfusion exit port 429 into the tissue. As infusaid is forced out of the reservoir 450, the diaphragm 452 will contract, thereby maintaining positive pressure within the reservoir 450. Once the diaphragm 452 returns to its fully contracted state, the reservoir 450 will no longer be pressurized, in which case, the infusaid will not be forced out of the reservoir 450, and perfusion ceases. If the ablation process has not been terminated, the reservoir 450 can be filled with more infusaid in order to pressurize the reservoir 450 and perfusion of the infusaid can again be commenced should it be necessary.

The ablation probe 410 can be used with the cannula 108 and the RF generator 104 to ablate and perfuse tissue in the same manner described above with respect to FIGS. 7A-7C. The main difference is that neither an external pump assembly nor a pump controller needs to be set up and connected to the ablation probe 410. Rather, only the infusaid source 346 need only be connected to ablation probe 410.

Figure 17:
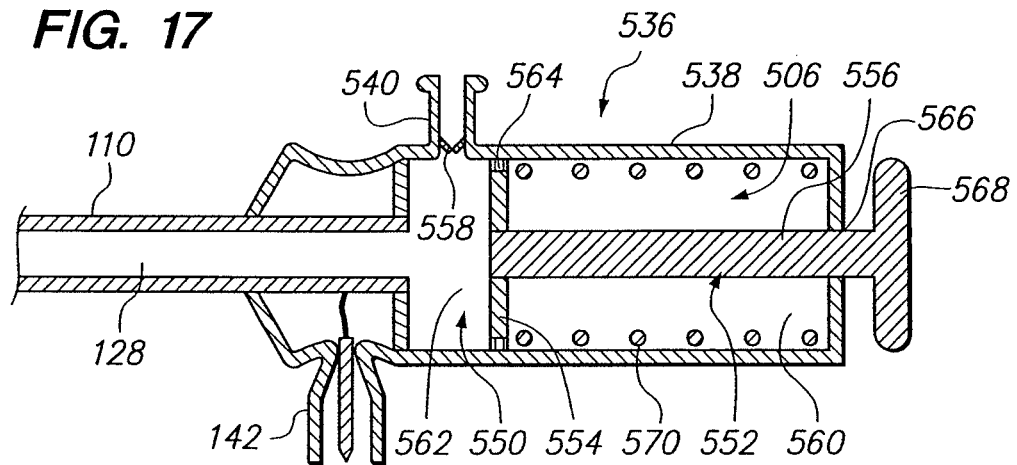
FIG. 17 is a cross-sectional view of the proximal end of yet another ablation probe that uses a plunger to pump infusaid through the ablation probe, particularly showing a plunger in its most distal position.
Figure 18:
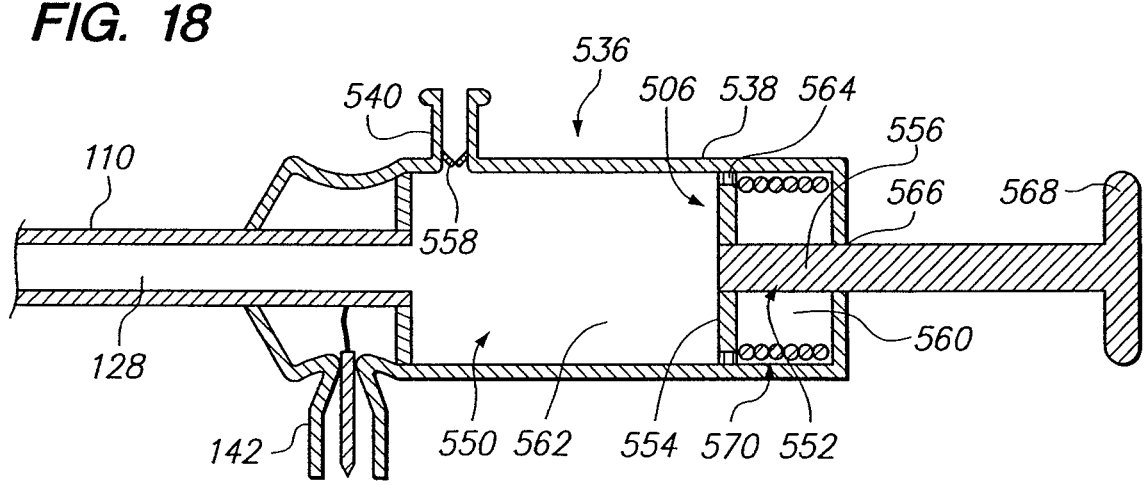
FIG. 18 is a cross-sectional view of the proximal end of the ablation probe of FIG. 17, particularly showing the plunger in its most distal position.

FIGS. 17 and 18 illustrate another connector assembly 536 that can be mounted to the proximal end of the ablation probe 410. The connector assembly 536 comprises the previously described RF port 142 to which the RF generator 104 can be connected, and a perfusion inlet port 540 to which a source of infusaid 346, such as a saline bag, can be connected via the tube 348 (shown in FIG. 8). The connector assembly 536 further comprises a manually activated pump assembly 506, which comprises a reservoir 550 and a plunger 552.

Specifically, the plunger 552 comprises a plunger head 554, which divides the reservoir 350 into proximal and distal reservoir regions 560 and 562. The plunger head 554 comprises a seal 564 that interfaces with the inner surface of the housing 538, such that the proximal and distal reservoir regions 560 and 562 are completely sealed from each other. The cross-section of the plunger head 554 and reservoir 550 are preferably circular, but can be other shapes as well, as long as a sufficient seal is created between the plunger head 554 and the inside surface of the housing 538.

The plunger 552 further comprises a plunger shaft 556, the distal end of which is mounted within the plunger head 554, and the proximal end of which extends out an opening 566 within the proximal end of the housing 538. A handle 568 is formed at the proximal end of the plunger shaft 552, so that a physician can pull the plunger 552 in the proximal direction by a physician, as illustrated in FIG. 15. As a result of the proximal displacement of the plunger head 554, the pressure within the distal reservoir region 562 decreases, and a portion of the infusaid within the infusaid source 346 is forced (sucked) into the distal reservoir region 562. Thus, when the plunger 552 is pulled to its most proximal position, the reservoir 550 will be completely filled with infusaid.

The pump assembly 506 further comprises a spring 570 disposed between the plunger head 554 and the proximal end of the housing 538. Thus, once the plunger handle 568 is released, the spring 570 will urge the plunger head 554 in the distal direction, thereby pressurizing the reservoir 550. A one-way check valve 558 is provided between the perfusion inlet port 540 and the reservoir 550 to prevent the infusaid in the reservoir 550 from being displaced back through the perfusion inlet port 540 and into the infusaid source 346.

Since the control valve 407 will be exposed to room temperature during the filling process, the perfusion exit port 429 will be totally closed at room temperature, thereby preventing infusaid from escaping out of the distal end of the ablation probe 410 when the plunger handle 568 is released. Optionally, the plunger 552 can include a locking mechanism (not shown) that locks the plunger 552 in placed once it is pulled back to its most proximal position. During the ablation process, the control valve 407 will be exposed to high temperatures, in which case, the perfusion exit port 429 will open. At this point, the infusaid, which is under positive pressure, will be forced out of the reservoir 550, through the perfusion lumen 128, and out of the perfusion exit port 429 into the tissue. As infusaid is forced out of the reservoir 350, the spring 570 will force the plunger head 554 to move in the distal direction, thereby maintaining positive pressure within the reservoir 550. Once the spring 570 returns to its uncompressed position, the plunger head 554 will stop moving, the reservoir 550 will no longer be pressurized, in which case, the infusaid will not be forced out of the reservoir 550, and perfusion ceases. If the ablation process has not been terminated, the plunger shaft 556 can be pulled back to fill the reservoir 550 with more infusaid, and then released in order to pressurize the reservoir 550 and commence perfusion of the infusaid again should it be necessary.

Figure 19:
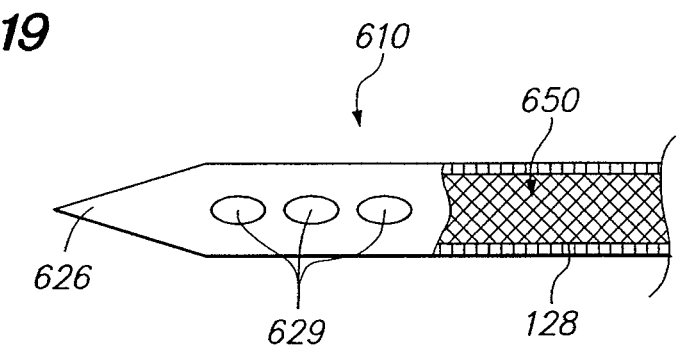
FIG. 19 is a partially cutaway side view of the distal end of yet another ablation probe that uses a wicking material to control the flow of infusaid through the ablation probe.

Referring now to FIG. 19, another ablation probe 610 that can be used with the RF generator 104 and any of the previously described pump assemblies will be described. The ablation probe 610 is similar to the previously described ablation probe 110, with the exception that the ablation probe 610 comprises a wicking material 650 disposed within the perfusion lumen 128. The wicking material 650 can be composed of any material that exhibits capillary action (e.g., cotton or fabric). In this manner, the wicking material 650 serves to regulate the flow of infusaid through the perfusion lumen 128.

Significantly, because the infusaid will travel through the perfusion lumen 128 in a slow and controlled manner due to the capillary action of the wicking material 650, the size of the perfusion exit ports at the distal end 124 of the shaft 120 can be made much larger, thereby preventing or minimizing clogging of the perfusion exit ports. In the illustrated embodiment, the ablation probe 610 is provided with relatively large side perfusion exit ports 629 out which the infusaid will seep from the wicking material 650. Because the infusaid will be perfused out of the side perfusion exit ports 629, the ablation probe 610 is provided with a close-ended needle electrode 626, thereby facilitating introduction of the shaft 120 through the tissue along a straight line. Alternatively or optionally, the previously described tapered needle electrode 126 can be provided.

In the case of ablation probes with needle electrode arrays, such as the ablation probe 210 illustrated in FIGS. 5 and 6, the wicking material can also be disposed within the lumens running through the needle electrodes, as well as the perfusion lumen extending through the shaft.

Any of the previously described pump assemblies, including a raised saline bag, can be used to pump the infusaid through the perfusion lumen 128. The ablation probe 610 can be used with the cannula 108 and the RF generator 104 to ablate and perfuse tissue in the same manner described above with respect to FIGS. 7A-7C. The main difference is that clogging of the perfusion exit ports will not be a significant concern when introducing the ablation probe 610 through the tissue.

Although particular embodiments of the inventions have been shown and described herein, there is no intention to the present inventions to the disclosed embodiments. Indeed, and it will be apparent to those skilled in the art that various changes and modifications may be made without departing from the scope of the inventions, as recited in the following claims.

What is claimed is:

1. An ablation probe, comprising: an elongate shaft having a proximal end and a distal end, wherein the distal end comprises a sharpened, open-ended, tapered tip ablative element; a perfusion lumen longitudinally extending within the shaft; at least one perfusion exit port in fluid communication with the perfusion lumen: a connector assembly, the connector assembly comprising a housing having a proximal end and a distal end, wherein the distal end of the housing comprises a threaded nut directly coupled to the proximal end of the shaft; a pump assembly disposed within the housing of the connector assembly, the pump assembly configured for pumping infusaid through the perfusion lumen and out the at least one perfusion exit port; a reservoir for storing the infusaid of the pump assembly; and a perfusion inlet port configured for transferring infusaid from an external source into the reservoir for storing the infusaid of the pump assembly; wherein the pump assembly comprises a plunger, the plunger having a pumping stroke that displaces the infusaid from the reservoir into the perfusion lumen, and a return stroke that displaces the infusaid from the external source into the reservoir; wherein the shaft is a unibody structure, and wherein the entire unibody structure is an electrically conductive material; and wherein the ablation probe is devoid of a secondary shaft that surrounds the unibody structure of the shaft.

2. The probe of claim 1, wherein the at least one perfusion exit port is disposed on a side of the perfusion lumen.

3. The probe of claim 1, wherein the at least one perfusion exit port is carried by the ablative element.

4. The probe of claim 1, wherein the pump assembly comprises a one-way check valve disposed between the perfusion inlet port and the reservoir.

5. The probe of claim 4, wherein the one-way check valve prevents the infusaid in the reservoir from being displaced back through the perfusion inlet port and into the external source.

6. The probe of claim 1, wherein the plunger comprises a plunger head adjacent the reservoir, the plunger head having a seal that interfaces with an internal surface of the housing of the connector assembly.

7. The probe of claim 6, wherein the plunger head comprises a cross-section having a circular shape.

8. The probe of claim 6, wherein the plunger comprises a plunger shaft having a distal end disposed on the plunger head, the plunger shaft further having a proximal end extending out an opening of the housing of the connector assembly.

9. The probe of claim 8, wherein the plunger comprises a plunger handle disposed on the proximal end of the plunger shaft.

10. The probe of claim 6, wherein the pump assembly comprises a spring disposed between the plunger head and the internal surface of the housing of the connector assembly, the spring configured for pressurizing the reservoir.

11. The probe of claim 1, wherein a side of the housing of the connector assembly comprises a radio frequency port in electrical communication with the ablative element.

12. The probe of claim 1, wherein the perfusion inlet port is disposed on a side of the housing of the connector assembly.

13. The probe of claim 1, wherein the connector assembly comprises a rigid metal material.

* * * * *